United States Patent
Kosar

(10) Patent No.: US 8,986,322 B2
(45) Date of Patent: Mar. 24, 2015

(54) APPARATUS FOR USING HYDRODYNAMIC CAVITATION IN MEDICAL TREATMENT

(75) Inventor: Ali Kosar, Istanbul (TR)

(73) Assignee: Sabanci Universitesi, Istanbul (TR)

( * ) Notice: Subject to any disclaimer, the term of this patent is extended or adjusted under 35 U.S.C. 154(b) by 211 days.

(21) Appl. No.: 13/698,045

(22) PCT Filed: May 14, 2010

(86) PCT No.: PCT/IB2010/052146
§ 371 (c)(1),
(2), (4) Date: Jan. 2, 2013

(87) PCT Pub. No.: WO2011/141775
PCT Pub. Date: Nov. 17, 2011

(65) Prior Publication Data
US 2013/0116703 A1    May 9, 2013

(51) Int. Cl.
| | |
|---|---|
| A61B 17/22 | (2006.01) |
| A61B 17/225 | (2006.01) |
| A61B 17/3203 | (2006.01) |
| A61B 19/00 | (2006.01) |

(52) U.S. Cl.
CPC ......... *A61B 17/2251* (2013.01); *A61B 17/3203* (2013.01); *A61B 19/5225* (2013.01); *A61B 2017/32032* (2013.01)
USPC ................................ 606/128; 606/130; 83/24

(58) Field of Classification Search
CPC ........................ A61B 17/2251; A61B 17/3203
USPC .................................................. 606/128, 130
See application file for complete search history.

(56) References Cited

U.S. PATENT DOCUMENTS 5,057,105 A * 10/1991 Malone et al. .................. 606/28
5,207,215 A * 5/1993 Rattner et al. .................... 601/4
(Continued)

FOREIGN PATENT DOCUMENTS

| | | |
|---|---|---|
| EP | 0 232 678 A2 | 8/1987 |
| WO | WO 00/69348 A1 | 11/2000 |

OTHER PUBLICATIONS

International Search Report, mailing date Nov. 2, 2011, for corresponding International Application No. PCT/IB2010/052146 with English translation.
(Continued)

*Primary Examiner* — Tuan V Nguyen
*Assistant Examiner* — Chima Igboko
(74) *Attorney, Agent, or Firm* — Intellectual Property Law Group LLP

(57) ABSTRACT

An apparatus for using hydrodynamic cavitation in medical treatment such as destroying kidney stones or killing infected cancer cells. This apparatus comprises a tank used as a container for a fluid, a compressor connected to the tank to maintain the input pressure of the fluid, a tubing wherein the fluid flows, a probe in which the cavitation occurs, a valve positioned inside the tubing, allowing the fluid to flow into the probe, a filter positioned inside the tubing, preventing the predetermined size particles flowing into the probe, a fitting connecting the probe to the tubing, a flowmeter measuring the volume flow rate of the fluid through the probe, an image capturing unit capturing the sequential images of bubbles growing and bubbles collapsing after the bubbles exit from the probe, a positioning assembly which adjusts the distance between the probe and the target surface, and a control and data acquisition unit.

16 Claims, 1 Drawing Sheet

(56) References Cited

U.S. PATENT DOCUMENTS

| | | | |
|---|---|---|---|
| 5,860,942 A * | 1/1999 | Cox | 601/155 |
| 2002/0050197 A1* | 5/2002 | Moutafis et al. | 83/24 |
| 2002/0177824 A1* | 11/2002 | Hajianpour | 604/276 |
| 2006/0194868 A1 | 8/2006 | Scholkens et al. | |
| 2006/0229550 A1* | 10/2006 | Staid et al. | 604/27 |
| 2007/0066978 A1* | 3/2007 | Schafer et al. | 606/128 |
| 2007/0179514 A1 | 8/2007 | Sengun | |
| 2007/0215068 A1* | 9/2007 | Langeder et al. | 122/451.2 |
| 2007/0228868 A1* | 10/2007 | Park et al. | 310/300 |
| 2008/0077056 A1* | 3/2008 | Kagosaki et al. | 601/2 |
| 2008/0114225 A1* | 5/2008 | Rabinovitz | 600/310 |
| 2008/0194868 A1 | 8/2008 | Kozyuk | |
| 2008/0194912 A1* | 8/2008 | Trovato et al. | 600/118 |
| 2009/0012536 A1* | 1/2009 | Rassman et al. | 606/133 |
| 2009/0054908 A1* | 2/2009 | Zand et al. | 606/130 |

OTHER PUBLICATIONS

Written Opinion, mailing date Nov. 2, 2011, for corresponding International Application No. PCT/IB2010/052146.

* cited by examiner

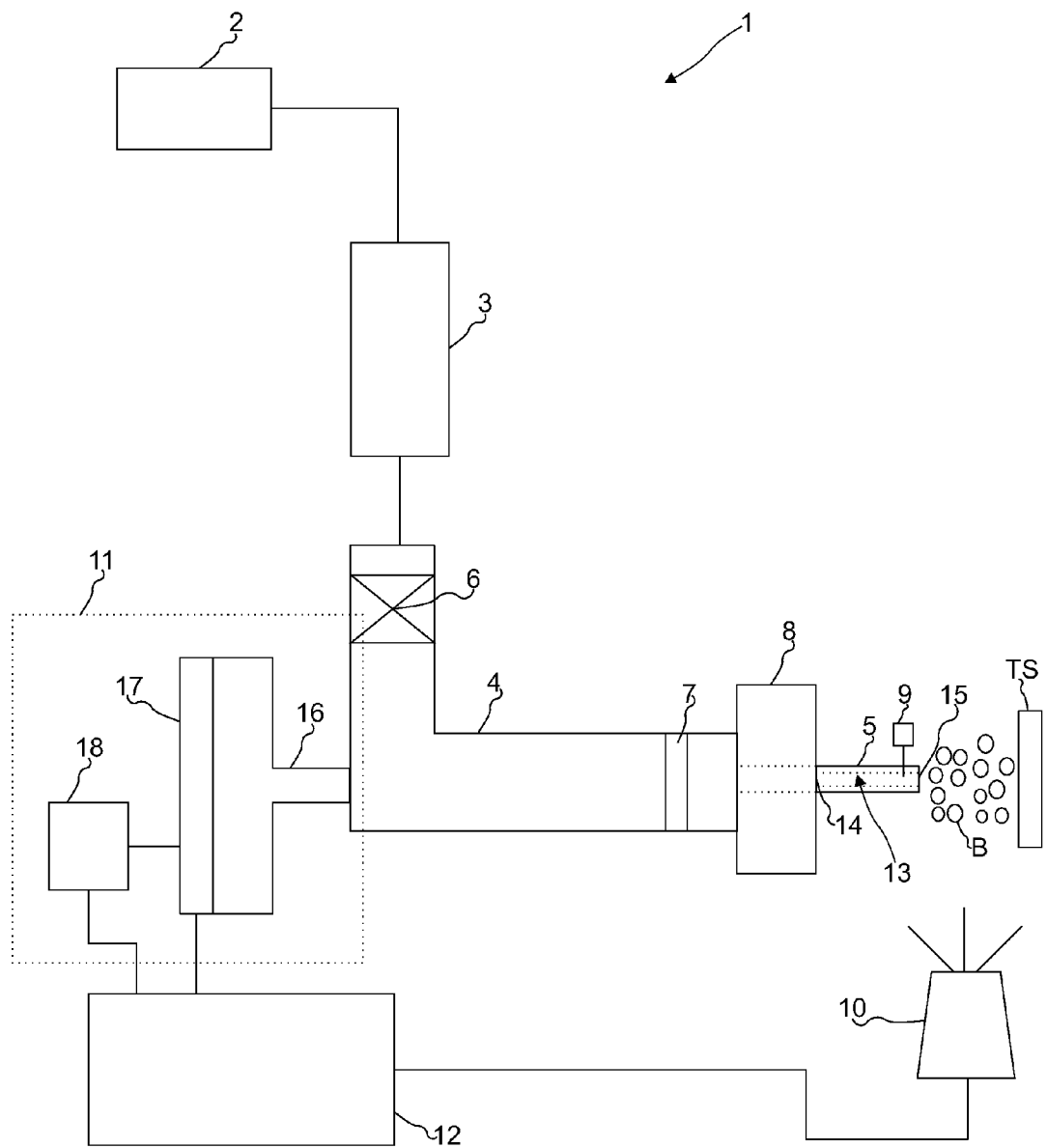

APPARATUS FOR USING HYDRODYNAMIC CAVITATION IN MEDICAL TREATMENT

CROSS-REFERENCE TO RELATED APPLICATIONS

This application is a U.S. National Phase application, under 35 U.S.C. §371, of International Application no. PCT/IB2010/052146, with an international filing date of May 14, 2010, and which is hereby incorporated by reference for all purposes.

BACKGROUND

The present invention relates to an apparatus for using the hydrodynamic cavitation in medical treatment such as destroying kidney stones or killing infected cancer cells.

Health care spending occupies a significant portion in the budgets of many countries and the spendings well exceed 4% of gross domestic products of many countries. These huge budgets allocated for health care spending should be wisely managed in order to find solutions for primary diseases threatening the health.

Hydrodynamic cavitation is typically initiated with local static pressure reduction below a critical value. Its effects on many turbomachinery have been investigated by numerous researchers in some articles and standard multiphase textbooks. It is known that every hydraulic device is susceptible to the damage caused by cavitation once the appropriate cavitating flow conditions are observed. In most cases, hydrodynamic cavitation is not desired since it limits the performance of the fluidic system, causes catastrophic damage and flow choking, generates acoustic noise, and lowers efficiency.

There are two main sources for creating cavitating flow; hydrodynamic and ultrasonic sources. The use of ultrasonic cavitation in ultrasonic treatment of cancerous tissues has been investigated by various researchers. This technique has been widely employed in cancer treatment. It is a non-invasing treatment, where some difficulties are faced to expose the treatment to the desired location. Ultrasonic cavitation associated with heating and electrochemical methods are expensive methods and much energy input is required to initiate bubbly cavitation and produce micro/nanobubbles.

The United States specification US20080194868 has disclosed a method in which the hydrodynamic cavitation is used for crystallizing a component, particularly active pharmaceutical compounds. The process disclosed in that document is used for purification of compounds. The application of the method is targeted in crystallization of pharmaceutical compounds and is applicable to macro scale.

The United States specification for U.S Pat. No. 5,860,942 has disclosed a dental water irrigator by employing hydrodynamic cavitation. The application of the method in said invention lies in removing plaque from the tooth surface. Hydrodynamic cavitation is employed to produce radicals and ions in water to eliminate dental diseases.

The United States specification US20060194868 has disclosed a device and method of generating micro bubbles in a liquid by using hydrodynamic cavitation. The application of the method in the said invention lies in mineral recovery applications, cleaning contaminated ground water and treatment of waste water. This process is generally used for purification.

SUMMARY

The objective of the present invention is to achieve a cost effective apparatus for using the hydrodynamic cavitation in medical treatment.

Another objective of the present invention is to achieve an energy effective apparatus for using the hydrodynamic cavitation in medical treatment.

BRIEF DESCRIPTION OF THE DRAWINGS

The apparatus for using the hydrodynamic cavitation in medical treatment realized in order to fulfill the objectives of the present invention is illustrated in the attached figures, where:

FIG. 1 is the schematic representation of the apparatus.

Elements shown in the figure are numbered as follows:
1. Apparatus for using the hydrodynamic cavitation in medical treatment
2. Tank
3. Compressor
4. Tubing
5. Probe
6. Valve
7. Filter
8. Fitting
9. Flowmeter
10. Image capturing unit
11. Positioning assembly
12. Control and data acquisition unit
13. Channel
14. Inlet region
15. Exit region
16. Strip
17. Heater
18. Power supply
B: Bubble
TS: Target surface Detailed Description:

An apparatus for using the hydrodynamic cavitation in medical treatment (1) comprising;
a tank (2) used as a container for a fluid,
a compressor (3) which is connected to the tank (2) in order to maintain the input pressure of the fluid,
a tubing (4) in which the fluid flows,
a probe (5) in which the cavitation occurs,
a valve (6), which is placed inside the tubing (4), allowing the fluid to flow into the probe (5),
a filter (7), which is placed inside the tubing (4), preventing the flow of particles of predetermined size into the probe (5),
a fitting (8) connecting the probe (5) to the tubing (4),
a flowmeter (9) measuring the volume flow rates of the fluid through the probe (5),
an image capturing unit (10) capturing the sequential images of bubble (B) growing and collapsing of the bubbles (B) after the bubbles (B) exit from the probe (5),
a positioning assembly (11) which adjusts the distance between the probe (5) and the target surface (TS) and,
a control and data acquisition unit (12).

The probe (5) comprising a channel (13) extends between two ends of the probe (5). Said channel (13) comprising of;
an inlet region (14) where the fluid enters into the channel (13) passing through a fitting (8) and,
an exit region (15) where the bubbles (B), formed as a result of the cavitation, exit from the channel (13) and exposed to the target surface (TS).

In a preferred embodiment of the invention the channel (13) is micro or nano scaled.

In a preferred embodiment of the invention the micro/nano channel (13) has a diameter of 0.5-250 µm. The channels (13) with nano/micro size inner diameters have a standard outside diameter so that they could be connected to the tubing (4) by using standard fittings (8). To prepare micro/nano channel (13), micro/nano size holes (900 nm-150 μm) are drilled by Focused Ion Beam or Electron Discharge (EDM) method. The one end of the resulting probe (5) of micron/nano size inner diameters is integrated to the tubing (4) with a small fitting (8) whereas the other end was targeted to target surface to be exposed to nano/micro scale bubbly cavitation. After the fabrication of the micro/nano probe (5), the channel (13) is filled with a nanofluid. In a preferred embodiment of the invention, copper or iron based nonofluid is used. The probe (5) is joule heated so that the nanofluid can evaporate. As a result of the evaporation, copper or iron nanoparticles are suspended in the nanofluid deposit on the channel (13) inner wall. The resulting nanostructures on the wall of nano/micro channel (13) facilitate cavitation so that lower inlet pressures are needed for the generation of micro/nano size bubbles (B). After this deposition, the probe (5) is cleaned in an ethanol solution. Cavitation is facilitated with these nanostructures and nano/micro bubbles (B) emerge from the porous nanostructured channel (13) walls.

The positioning assembly (11) comprising,
a strip (16) which is fixed at the end of the tubing (4),
a heater (17) in contact with the strip (16) and
a power supply (18) giving necessary electrical power to the heater (17).

In a preferred embodiment of the invention the strip (16) is a T-shaped silicon strip (16) which is fixed at two ends and is brought to contact with the tubing (4), which is connected to probe (5). The heater (17) is deposited to the silicon layer of the strip (16). The power supply (18) gives the necessary electrical power to the heater (17). When electrical power is given to the heater (17) from a power supply (18), the silicon strip (16) bends due to thermal expansion following temperature rise, which leads to push the tubing (4) towards the target surface (TS) and thus to adjust the distance between the probe (5) and the target surface (TS). The heater (17) measures the temperature of the strip (16) surface and transmits the signal comprising the temperature data of the strip (16) surface to the control and data acquisition unit (12).

The control and data acquisition unit (12) is connected to the image capturing unit (10), heater (17) and power supply (18). It (12) receives the image data from the image capturing unit (10) and determines the optimal distance needed between the probe (5) and the target surface (TS) for an effective damage on the target surface (TS). Said control and data acquisition unit (12) receives the temperature data of the strip (16) surface from the heater (17). By the help of the image data, the control and data acquisition unit (12) determines the distance and activates the power supply (18). After the power supply (18) is activated, the control and data acquisition unit (12) controls the bending of the strip (16) in order to adjust said determined optimal distance between probe (5) and the target surface (TS) by using the temperature input coming from the heater (17).

When the apparatus (1) is started the compressor (3) brings the fluid in the tank (2) into the predetermined pressure. Then the valve (6) is opened and the fluid in the tank (2) starts to flow in the tubing (4). Before the fluid enters into the channel (13), it is filtered from the undesirable objects which have predetermined sizes by the filter (7). Thus, clogging of the channel by large particles in the fluid is prevented. After the fluid enters into the channel (13), it flows through the channel (13) and experiences severe and sudden pressure drop. As a result, local static pressure of the fluid decreases. If the pressure decreases to a certain critical value under suitable conditions, bubbles (B) start to form inside the fluid and emerge from the channel (13) wall. At the exit region (15) of the channel (13), the bubbly cavitation is observed. Then, the bubbles (B) exit the channel (13) and hit the target surface (TS). While they are exiting the channel (13), their images are captured by an image capturing unit (10) in order to control the sizes of the bubbles (B) and the distance between the probe (5) and the target surface (TS). The captured image data are sent to the control and data acquisition unit (12). The control and data acquisition unit (12) determines the most effective distance between the probe (5) and the target surface (TS) for destroying the target surface (TS) by using received image data. If the distance between the probe (P) and the target surface (TS) is not close enough to each other, said unit (12) activates the power supply (18), and heater (17) starts to heat the silicon layer of the strip (16). While the temperature of the silicon strip (16) increases, it starts to bend which results in moving of the tubing (4), as well as connected probe (5). While the heater (17) is operating, the temperature data are sent to the control and data acquisition unit (12) by the heater (17). Said control and the data acquisition unit (12) controls the amount of bending of the strip (16) by using the temperature input and adjusts the effective destroying distance between the target surface (TS) and the probe (5) along with the feedback (image data) obtained from the image capturing unit (10).

The bubbles (B) caused by hydrodynamic bubbly cavitation are highly destructive on surfaces once they are localized. Because of this reason, they are utilized for a variety of treatments such as destroying kidney stones or killing infected cancer cells.

In a preferred embodiment of the invention the fluid used in the apparatus (1) is the deionized water and phosphate buffered saline (PBS). Deionized water is used for kidney stones treatment, where the environment is compatible with this fluid, while for killing cancerous cells the fluid should be PBS, which is a compatible liquid for cell cultures.

In a preferred embodiment of the invention, the image capturing unit (10) is a charged coupled device (CCD) camera.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. An apparatus for using hydrodynamic cavitation in medical treatment comprising:
 a tank used as a container for a fluid,
 a compressor which is connected to the tank in order to maintain an input pressure of the fluid,
 a tubing in which the fluid flows,
 a probe which is configured for cavitation,
 a valve, which is positioned inside the tubing, allowing the fluid to flow into the probe,
 a filter, which is positioned inside the tubing, preventing a predetermined size particles flow into the probe,
 a fitting connecting the probe to the tubing,
 a flowmeter measuring a volume flow rate of the fluid through the probe,
 an image capturing unit capturing a plurality of sequential images of bubbles growing and collapsing of the bubbles after the bubbles exit from the probe,
 a positioning assembly which adjusts a distance between the probe and a target surface and,
 a control and data acquisition unit,
 wherein the positioning assembly comprising;
 a strip which is fixed at an end of the tubing,
 a heater in contact with the strip and a power supply giving necessary electrical power to the heater.

2. An apparatus according to claim 1, wherein the used strip is a T-shaped silicon strip.

3. An apparatus according to claim 1, wherein the control and data acquisition unit is connected to the image capturing unit, heater and power supply.

4. An apparatus according to claim 3, wherein the control and data acquisition unit receives an image data from the image capturing unit and determines an optimal distance needed between the probe and the target surface for an effective damage on the target surface.

5. An apparatus according to claim 4, wherein the control and data acquisition unit receives a temperature data of a surface of the strip from the heater.

6. An apparatus according to claim 5, wherein the control and the data acquisition unit controls the amount of bending of the strip by using the temperature data and adjusts the effective destroying distance between the target surface and the probe along with the image data obtained from the image capturing unit.

7. An apparatus according to claim 3, wherein the control and data acquisition unit receives a temperature data of a surface of the strip from the heater.

8. An apparatus according to claim 7, wherein the control and the data acquisition unit controls the amount of bending of the strip by using the temperature data and adjusts the effective destroying distance between the target surface and the probe along with the image data obtained from the image capturing unit.

9. An apparatus for using hydrodynamic cavitation in medical treatment comprising;
- a tank used as a container for a fluid,
- a compressor which is connected to the tank in order to maintain an input pressure of the fluid,
- a tubing in which the fluid flows,
- a probe which is configured for cavitation,
- a valve, which is positioned inside the tubing, allowing the fluid to flow into the probe,
- a filter, which is positioned inside the tubing, preventing a predetermined size particles flow into the probe,
- a fitting connecting the probe to the tubing,
- a flowmeter measuring a volume flow rate of the fluid through the probe,
- an image capturing unit capturing a plurality of sequential images of bubbles growing and collapsing of the bubbles after the bubbles exit from the probe,
- a positioning assembly which adjusts a distance between the probe and a target surface and,
- a control and data acquisition unit;

wherein the probe comprising a channel extends between two ends of the probe comprising of:
- an inlet region where the fluid enters into the channel passing through the fitting and,
- an exit region where the bubbles, formed as a result of the cavitation, exit from the channel and exposed to the target surface;

wherein the positioning assembly comprising;
- a strip which is fixed at an end of the tubing,
- a heater in contact with the strip and
- a power supply giving necessary electrical power to the heater.

10. An apparatus according to claim 9, wherein the channel is micro or nano scaled.

11. An apparatus according to claim 10, wherein micro or nano size holes are drilled to the probe by a Focused Ion Beam or Electron Discharge (EDM) method while preparing the channel.

12. An apparatus according to claim 11, wherein the used strip is a T-shaped silicon strip.

13. An apparatus according to claim 10, wherein the used strip is a T-shaped silicon strip.

14. An apparatus according to claim 9, wherein the used strip is a T-shaped silicon strip.

15. An apparatus according to claim 9, wherein the control and data acquisition unit is connected to the image capturing unit, heater and power supply.

16. An apparatus according to claim 15, wherein the control and data acquisition unit receives an image data from the image capturing unit and determines an optimal distance needed between the probe and the target surface for an effective damage on the target surface.

* * * * *